United States Patent
Dubner et al.

(10) Patent No.: US 6,225,509 B1
(45) Date of Patent: May 1, 2001

(54) ALLYL ALCOHOL HYDROFORMYLATION

(75) Inventors: Walter S. Dubner, Wilmington, DE (US); Wilfred Po-sum Shum, West Chester, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/478,480

(22) Filed: Jan. 6, 2000

(51) Int. Cl.⁷ .................................................. C07C 45/00
(52) U.S. Cl. .............................. 568/454; 568/451
(58) Field of Search ..................... 568/451, 454

(56) References Cited

U.S. PATENT DOCUMENTS

| 4,215,077 | 7/1980 | Matsumoto et al. . |
| 4,238,419 | 12/1980 | Matsumoto et al. . |
| 4,567,305 | 1/1986 | Matsumoto et al. . |
| 4,678,857 | 7/1987 | Dureanleau et al. . |

FOREIGN PATENT DOCUMENTS

| H6-279344 | 10/1994 | (JP) . |
| H6-279345 | 10/1994 | (JP) . |

OTHER PUBLICATIONS

Kamer et al, "Designing Ligands with the Right Bite" Sep., 1998, Chemtech P. 27–33.

*Primary Examiner*—Johann Richter
*Assistant Examiner*—J. Parsa
(74) *Attorney, Agent, or Firm*—William C. Long

(57) ABSTRACT

Hydroxybutyraldehyde is formed by hydroformylation of allyl alcohol using a catalyst comprised of a rhodium complex and a ligand such as DIOP, the concentration of CO in the reaction liquid is maintained above about 4.5 mg. mols/liter.

6 Claims, 3 Drawing Sheets

ALLYL ALCOHOL HYDROFORMYLATION

BACKGROUND OF THE INVENTION

1. Field of the Invention

The present invention relates to the hydroformylation of allyl alcohol to product comprising mainly 4-hydroxybutyraldehyde (herein HBA) using a rhodium complex catalyst and a bidendate diphosphine ligand such as a (isopropylindene-2,3-dihydroxy-1,4-diphenylphosphine) butane (herein DIOP) ligand having a bite angle of 100–120 degrees, under reaction conditions wherein a relatively high liquid phase concentration of carbon monoxide is maintained during the reaction.

2. Description of the Prior Art

It is known to react allyl alcohol with a carbon monoxide and hydrogen mixture to form hydroxybutyraldehyde; various catalyst formulations have been employed, most notably a rhodium complex together with a phosphine ligand. Commonly employed phosphine ligands are trisubstituted phosphines such as triphenyl phosphine. Patents which are illustrative of such technologies include U.S. Pat. Nos. 4,567,305, 4,215,077, 4,238,419 and the like.

The hydroformylation of allyl alcohol to hydroxybutyraldehyde using rhodium complex catalysts and DIOP ligand is shown in the art, notably in Japan Kokai 06-279345 and 06-279344.

Butanediol is produced commercially by a process which involves hydroformylation of allyl alcohol to 4-hydroxybutyraldehyde and hydrogenation of the 4-hydroxybutraldehyde to 1,4- butanediol (herein BDO). Usually some methyl propanediol (herein MPD), itself a useful material, is formed from methyl hydroxypropionaldehyde (HMPA) also formed in the hydroformylation. A severe disadvantage of prior processes has been the formation of $C_3$ products such as normal propanol, propionaldehyde, and the like during the hydroformylation. Formation of these materials effectively represents a yield loss in the process which can have a severe adverse effect on the process economics.

SUMMARY OF THE INVENTION

It has now been found that in the hydroformylation of allyl alcohol using a rhodium complex catalyst in combination with a bidendate diphosphine ligand having a bite angle in the range 100–120 degrees, such as DIOP ligand, unlike systems involving other ligands the concentration of carbon monoxide (CO) in the liquid reaction mixture is critical insofar as reducing the undesirable make of $C_3$ co-products. Specifically, the CO concentration must be maintained above about 4.5 mg. mols/liter of reaction liquid, preferably above about 5.0 mg. mols/liter in order to achieve high 4-hydroxybutyaldehyde selectivities.

BRIEF DESCRIPTION OF THE DRAWING

The attached drawings are graphical representations showing various process results as a function of the concentration of CO in the reaction liquid.

DETAILED DESCRIPTION

The present invention provides an improved process for the hydroformylation of allyl alcohol to 4-hydroxybutyraldehyde. In accordance with known procedures, a rhodium complex catalyst is employed. See, for example, U.S. Pat. Nos. 4,238,419, 4,678,857, 4,215,077, 5,290,743 and the like.

Essential to the process of the invention is the use of a bidendate diphosphine ligand having a bite angle of 100–120 degrees, such as DIOP ligand, in conjunction with the rhodium complex catalyst. DIOP is 2,3-O-Isopropylidene-2,3-dihydroxy-1,4-bis(diphenylphosphino)-butane and has a 105 degree bite angle. Either enantiomer or mixtures of the enantiomers can be used. Generally the use of at least 1 mol bidendate diphosphine per mol of rhodium is used, preferably at least 1.5 mols bidendate diphosphine per mol rhodium is used. Little advantage is gained through use of 4 or more mols of bidendate diphosphine per mol rhodium, the preferred range is about 1.5–3 mols diphosphine/mol rhodium.

In addition to DIOP, suitable bidendate diphosphine ligands include the xanthene-based diphosphines such as xantphos which is 9,9-Dimethyl-4,6-bis (diphenylphosphino)xanthene and 2,7-Di-tert-butyl-9,9-dimethyl-4,6-bis(diphenylphosphino)xanthene. Xantphos has a bite angle of 112 degrees. Further information on the bite angle of bidentate ligands is given in "Designing Ligands with the Right Bite", Chemtech, September 1998, pages 27–33.

The hydroformylation is carried out by passing a $CO/H_2$ gas mixture through a reaction liquid comprised of allyl alcohol and the catalyst system at reaction conditions. Usually a solvent is used, such as an aromatic hydrocarbon. Benzene, toluene and xylenes are preferred. Generally allyl alcohol concentrations in the range of about 5–40% by weight in the solvent are useful, it has been found that the lower concentrations in the range of 5–10% favor higher normal to iso product ratios. Generally gas mixtures having $H_2/CO$ mol ratios in the range 10/1 to about 1/2 can be employed. The use of lower relative amounts of hydrogen, eg 5/1 to about 1/1 mols $H_2/Co$ are especially useful; at the higher levels of hydrogen some by-product formation tends to occur.

Figure 1:
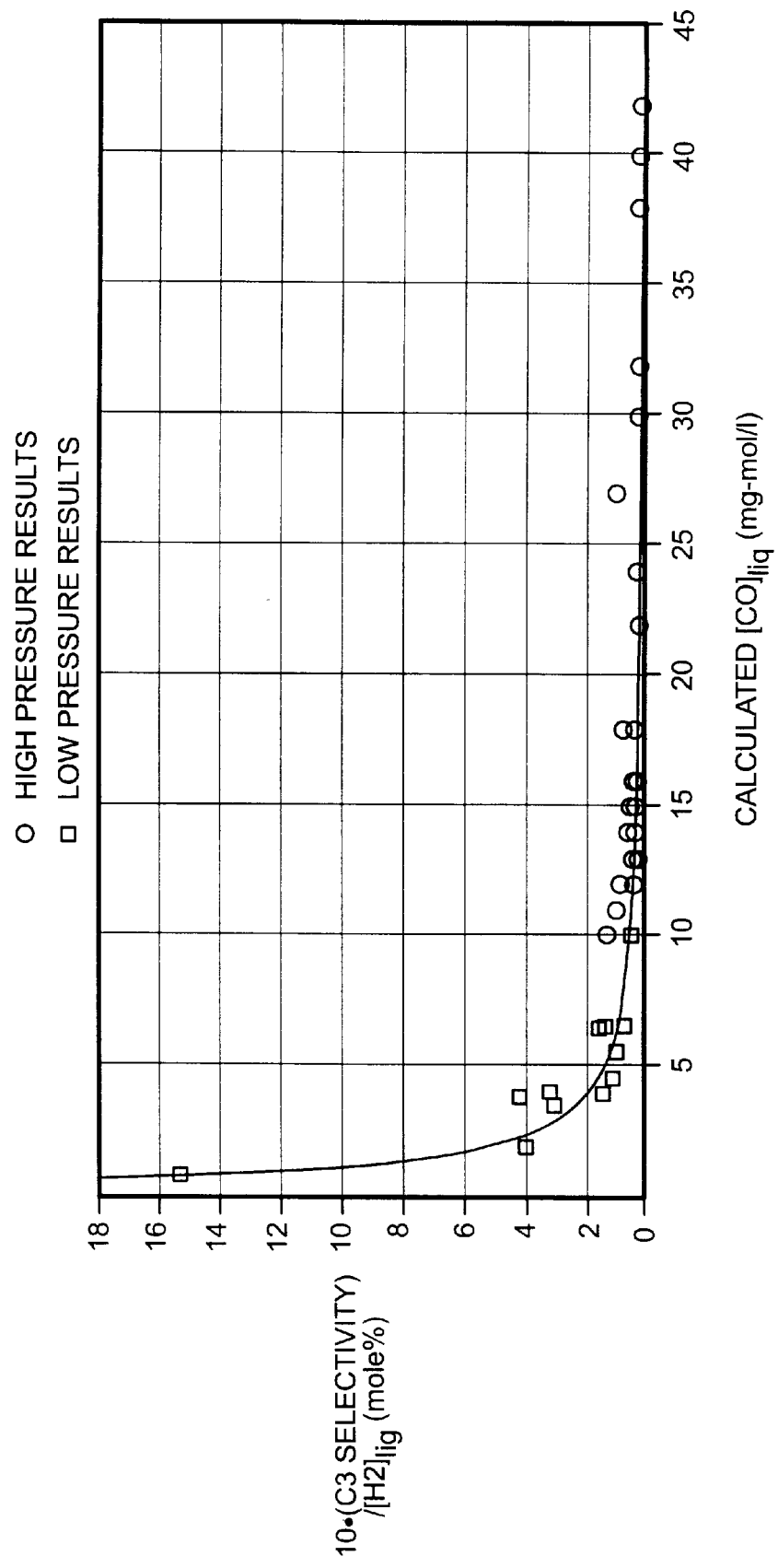
FIG. 1 shows the effect of increasing CO concentration on the undesirable make of $C_3$ by-products.

The dramatic effect of concentration of CO in the reaction liquid on the undesirable make of $C_3$ by-products is illustrated in the attached FIG. 1. It can be seen from the graphical representation of FIG. 1 that the make of undesirable $C_3$ products rises very sharply at the lower concentrations of CO in the reaction liquid.

Figure 2:
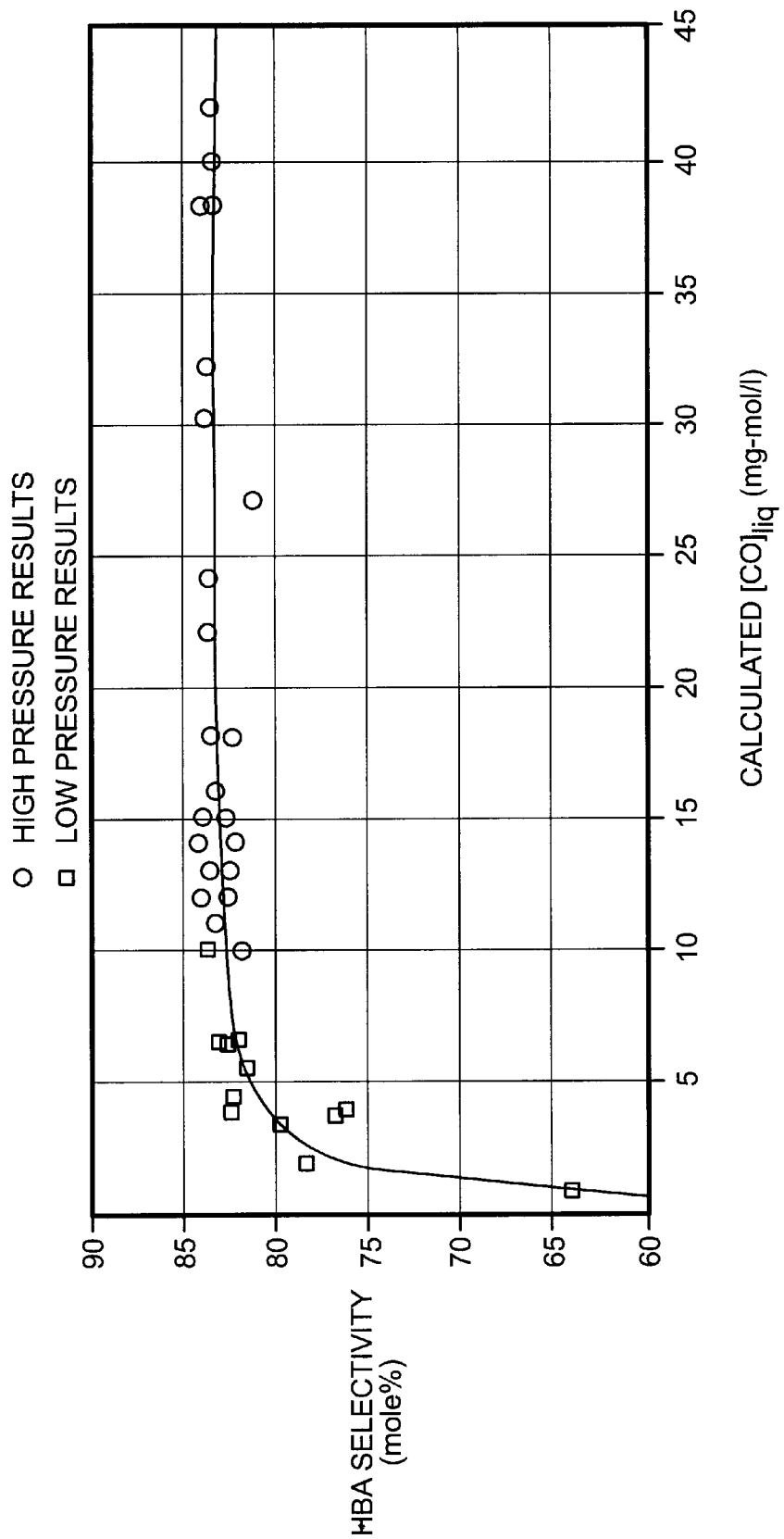
FIG. 2 shows the effect of CO concentration on reaction selectivity to 4-hydroxybutyraldehyde.

FIG. 2 is a similar plot of the reaction selectivity to 4-hydroxybutyraldehyde as a function of CO concentration in the liquid and it can be seen that 4-hydroxybutyraldehyde selectivity increases rapidly until leveling off at the higher CO concentration, eg at CO concentrations above about 8 mg. mols/liter.

Figure 3:
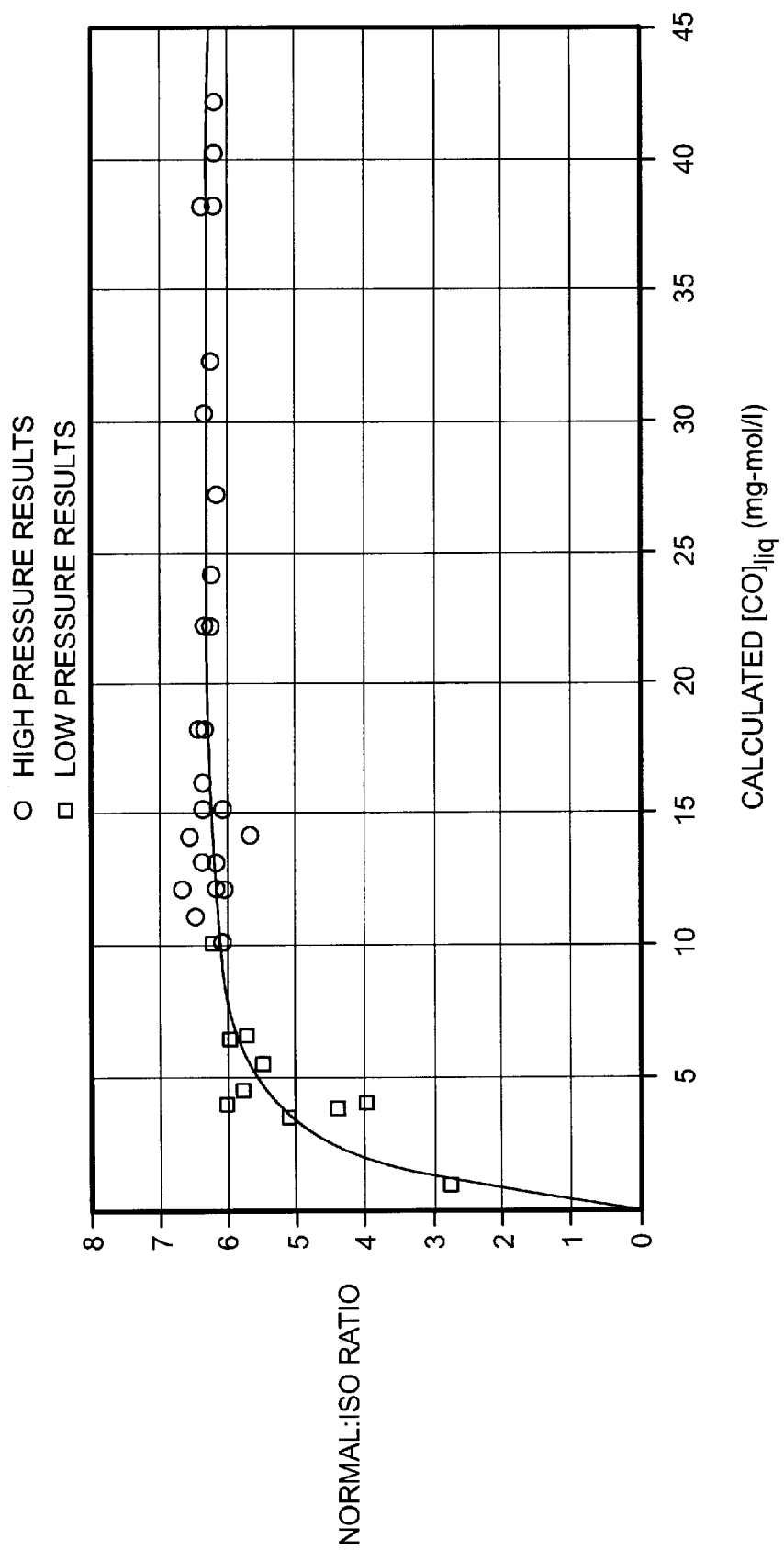
FIG. 3 shows the effect of CO concentration on the ratio of normal (HBA) to branched products (HMPA) formed during the reaction. In each case DIOP was the bidendate ligand.

In the hydroformylation of allyl alcohol, the production of the linear 4-hydroxybutyraldehyde is preferred over the branched or iso product methyl hydroxypropionaldehyde (HMPA). A further advantage of the present invention can be seen by reference to FIG. 3 which is a graphical representation of the normal/iso product ratio as a function of CO concentration in the reaction liquid. It can be seen that the normal/iso ratio increases with increasing CO concentrations in the reaction liquid, reaching a relative plateau at CO concentrations above about 8 mg. mols/liter.

In accordance with the present invention, the allyl alcohol hydroformylation is carried out using a rhodium complex catalyst and the bidendate diphosphine ligand such that the value of $[CO]_{liq}$, defined by formula (I), given below, is maintained above 4.5 mg. mols/liter in substantially the entire reaction zone in which the hydroformylation reaction proceeds:

$$[CO]_{liq} = (31.49 - 0.179T + 3.309 \times 10^{-4} T^2) P_{CO} - \alpha \left(\frac{\mu}{T}\right)^{0.5} \left(\frac{r_{CO}}{K_V}\right) \quad (1)$$

wherein T is the reaction temperature (°K.) and is selected to be within the range of 323° K. to 353° K. (absolute temperature), $P_{co}$ is the logarithmic mean (in atmospheres, absolute) between the partial pressure of carbon monoxide in the feed gas entering the reactor in which the hydroformylation reaction is conducted and the partial pressure of carbon monoxide in the effluent gas leaving said reactor and is within the range of 0.01 to 3.0 absolute atmosphere, $\alpha$ is 3,500 for the cases in which mechanical stirring is performed within the reactor and 1,200 for all other cases, $\mu$ is the viscosity (centipoises, cp) of the reaction mixture at the reaction temperature and is selected to be within the range of 0.1 to 4.0 cp, $r_{co}$ is the rate (moles/liter-hour) of consumption of carbon monoxide in the hydroformylation reaction and is selected to be within the range of from 0.001 to 10 moles/liter-hour, and Kv is the rate (millimoles/liter-hour) of absorption of oxygen in water as determined separately from and independently of the hydroformylation reaction by measuring the rate of oxidation of an aqueous sodium sulfite solution with air at 25° C. at the operating pressure in the reactor to be used for the hydroformylation reaction and is typically within the range of 5 to 500 millimoles/liter-hour, provided that in cases where the reactor in which the hydroformylation reaction is carried out comprises a plurality of reaction chambers, each reaction chamber is regarded as a single reactor and the above constant and variables should be selected accordingly for each reaction chamber.

The value of $[CO]_{liq}$ defined by the above formula (I) is considered to be closely related to the amount of carbon monoxide present in the reaction mixture. By maintaining the value of $[CO]_{liq}$ above 4.5 mg. mols/liter it is possible to conduct the continuous hydroformylation of allyl alcohol to form 4-hydroxybutyraldehyde in a highly selective fashion.

The rate of consumption of carbon monoxide as expressed by $r_{co}$ in the above formula (I) can be determined easily by measuring the rate of flow of the feed gas entering the hydroformylation reactor and that of the effluent gas leaving said reactor, as well as the carbon monoxide concentration in the feed gas and that in the effluent gas. The value of this $r_{co}$ can also be determined from the rate of feeding allyl alcohol into the hydroformylation reactor, the concentration of unreacted allyl alcohol in the reaction mixture and the selectivity of the hydroformylation reaction (total selectivity toward HBA and HMPA).

The value of Kv is determined by measuring, independently of and separately from the hydroformylation reaction, the rate of oxidation of an aqueous sodium sulfite solution with air at 25° C. in the same reactor that is to be used for said hydroformylation reaction or in a reactor of the same type. The method of measurement for this purpose has already been established and the details thereof can be found, for instance in Industrial and Engineering Chemistry, Vol. 48, No. 12, pages 2209–2122 (1956). This Kv value depends on the method of supplying the feed gas and the shape of the hydroformylation reactor and also is subject to the influence of the stirring power of the reactor, the shape of the impeller, the method of distribution of the feed gas, and so on. Therefore, in making the Kv value determination, it is of course necessary to employ the same conditions as the hydroformylation reaction conditions, except that the same reactor that is to be used in the hydroformylation or a reactor of the same construction is charged with an aqueous sodium sulfite solution and that air is fed into said reactor, in place of the hydrogen-carbon monoxide mixed gas, at the same linear velocity as under the hydroformylation reaction conditions, while maintaining the inside temperature at 25° C., under atmospheric pressure. The measurement for determining the Kv value for the hydroformylation reactor can also be conducted by using a reactor of the same type as the hydroformylation reactor but of smaller size.

The value of $\alpha$ is 3,500 in cases where mechanical stirring is performed within the hydroformylation reaction vessel by means of an impeller or the like, whereas it is 1,200 in cases where mechanical stirring is not performed, for instance, in the case of a bubble column.

The value of $\mu$ which is the viscosity of the reaction mixture at the reaction temperature, can be determined by conventional methods.

In the present invention, it is required to select the values of T, $P_{co}$, $\alpha$, $\mu$, $r_{co}$ and Kv interrelatedly within the respective ranges specified hereinabove so that the value of $[CO]_{liq}$ defined by formula (I) can be maintained above 4.5 mg. mols/liter and preferably above about 5.0 mg. mols/liter in substantially the entire zone in which the hydroformylation reaction proceeds. By taking the above measures, markedly improved effects, such as those mentioned above, can be produced. If the value of $[CO]_{liq}$ is smaller than 4.5 mg. mols/liter, the rate of formation of undesirable by-products tends to increase and the rate of the desired reaction tends to decrease, hence the yield of 4-hydroxybutyraldehyde tends to decrease. In that case, the life of the rhodium complex catalyst may also be shortened.

In prior art procedures where the rhodium complex and DIOP ligand condensation was used, eg. Japan Kokai 06-279344 and 06-279345, maximum values of $[CO]_{liq}$ of about 4.3 mg. mols/liter were used. Higher concentrations of CO are used in accordance with the present invention.

It is also advantageous to regulate the liquid phase hydrogen concentration in accordance with the following equation:

$$[H_2]_{liq} = (-2.79 + 9.22 \times 10^{-3} T + 3.27 \times 10^{-5} T^2) P_{H2} - \alpha \left(\frac{\mu}{T}\right)^{0.5} \left(\frac{r_{H2}}{K_V}\right),$$

where $[H_2]_{liq}$ is concentration in millimole liter, T is in degrees Kelvin, $P_{H2}$ is log-mean average partial pressures of hydrogen using inlet and outlet gas composition in atmospheres, $\alpha$ is 3332, $\mu$ is the reaction solution viscosity in cP, r is the respective reaction rate in moles/liter-h and $K_v$ is the rate of oxygen absorption in water as independently measured by a standard sodium sulfite test in units of millimole/liter-h.

By way of illustration, a series of allyl alcohol hydroformylation experiments were conducted as follows:

Catalyst solution comprised of rhodium and DIOP ligand in toluene was continuously fed to a well-mixed agitated reactor along with allyl alcohol, carbon monoxide and hydrogen. Rhodium and DIOP concentration in the catalyst solution can be independently varied to achieve the desired reaction rate, but a minimum DIOP/Rh concentration of between 1 and 1.5 mole ratio should be targeted. Other ligands such as triphenyl phosphine (TPP) and diphenyl phosphine (DPB) may be present. Rhodium and DIOP concentrations were measured in the catalyst solution feeding the reactor. Other bidentate phosphine ligands with certain "bite-angle" considerations (greater than 100°), such as Xantphos were also shown to be an effective substitute for DIOP.

Carbon monoxide, hydrogen and an inert gas was independently fed to the reactor, to achieve independent control of their respective concentrations. This flow control, along with total reaction pressure, determined the respective feed gas partial pressures.

The reaction may be carried out over a wide range of temperatures to achieve the desired reaction rate. For this work, temperature was kept at 145 degrees Fahrenheit. Liquid product was continuously removed from the reactor to determine reaction rate and product selectivity, and gas sampling was used to determine exit gas composition.

Using these analyses, standard techniques were used to develop correlations between dissolved gas composition and product selectivity for the allyl alcohol hydroformylation reaction.

Table 1 shows results from experiments carried out using this experimental procedure and analysis technique.

TABLE 1

DIOP Experiments

| $P_{co}$ (psia) | $P_{H2}$ (psia) | $[CO]_{liq}$ (mmol/l) | $[H2]_{liq}$ (mmol/l) | Rh (ppm) | DIOP (wt %) | k ($h^{-1}$) | n/i | HBA (mol %) | $C_3$ (mol %) |
|---|---|---|---|---|---|---|---|---|---|
| 3 | 27 | 1 | 6.5 | 142 | 0.21 | 6.5 | 2.8 | 64 | 10 |
| 8 | 30 | 3.8 | 7.2 | 115 | 0.09 | 6.5 | 4.4 | 77 | 3 |
| 8 | 26 | 4 | 6.3 | 145 | 0.21 | 5.5 | 4.0 | 76 | 2 |
| 12 | 29 | 6.5 | 7.3 | 160 | 0.21 | 3.5 | 5.8 | 82 | 0.5 |
| 11 | 14 | 6.5 | 3.5 | 160 | 0.21 | 1.8 | 6.0 | 83 | 0.3 |
| 17 | 21 | 10 | 5.5 | 172 | 0.26 | 1.9 | 6.2 | 84 | 0.3 |
| 27 | 44 | 15 | 11 | 190 | 0.21 | 2.6 | 6.4 | 84 | 0.2 |
| 28 | 120 | 15 | 31 | 190 | 0.18 | 4.0 | 6.3 | 83 | 1.5 |
| 52 | 92 | 30 | 24 | 200 | 0.16 | 2.3 | 6.4 | 84 | 0.2 |

The results given above are presented graphically along with data from analogous runs in the attached Figures and clearly illustrate the advantages of the invention. In the above table, the first three runs are at CO concentrations well below the 4.5 mmol/l lower limit of the present invention and thus are comparative.

Additional hydroformylation experiments were carried out with other bidentate diphosphine ligands having a bite angle of 100–120 degrees. The experiment in each case was a batch run carried out with toluene solvent and was run at 65° C. to completion. The rhodium concentration was 200 ppm in all runs. In Runs 2-1, 2-3, 2-4 and 2-5, the mol ratio of ligand to rhodium was 4:1, in the other runs the ratio was 2:1. Total pressure was 300 psig except for runs 2-2, 2-6 and 2-11 (200 psig) and run 2-12 (120 psig). Feed concentration of allyl alcohol in toluene was 17.8 wt % for Runs 2-1, 2-2, 2-4, 2-8, 2-11 and 2-12, 6.3 wt % for Runs 2-3, 2-5, 2-6 and 2-10, 23 wt % for Run 2-7 and 9.8 wt % for Run 2-9. In all cases CO concentration in the liquid phase was above 4.5 mg. mols/liter.

The following table shows the results obtained.

TABLE 2

| Run | Ligand (wt %) | $P_{co}$ (psia) | $P_{H2}$ (psia) | n/i Ratio | % HBA | $C_3$ (mol %) |
|---|---|---|---|---|---|---|
| 2-1 | 0.30 | 143 | 143 | 10 | 88.4 | 2.8 |
| 2-2 | 0.15 | 93 | 93 | 8.5 | 87.1 | 2.7 |

TABLE 2-continued

| Run | Ligand (wt %) | $P_{co}$ (psia) | $P_{H2}$ (psia) | n/i Ratio | % HBA | $C_3$ (mol %) |
|---|---|---|---|---|---|---|
| 2-3 | 0.30 | 143 | 143 | 16.7 | 91.0 | 3.5 |
| 2-4 | 0.58 | 143 | 143 | 8.8 | 87.5 | 2.6 |
| 2-5 | 0.58 | 143 | 143 | 13.4 | 89.9 | 3.4 |
| 2-6 | 0.14 | 93 | 93 | 7.7 | 87.4 | 1.2 |
| 2-7 | 0.22 | 143 | 143 | 6.7 | 86.3 | 0.9 |
| 2-8 | 0.22 | 143 | 143 | 7.1 | 87.2 | 0.5 |
| 2-9 | 0.22 | 143 | 143 | 7.6 | 87.8 | 0.7 |
| 2-10 | 0.22 | 143 | 143 | 8.2 | 88.4 | 0.8 |
| 2-11 | 0.22 | 93 | 93 | 6.8 | 86.7 | 0.5 |
| 2-12 | 0.22 | 53 | 53 | 6.6 | 86.4 | 0.6 |

In runs 2-1 through 2-3, the ligand used was 9,9-Dimethyl-4,6-bis(diphenylphosphino)xanthene (Xantphos with a bite angle of 112 degrees). In runs 2-4 and 2-5, the ligand used was 2,7-di-tert-butyl-9,9-dimethyl-4,6-bis (diphenylphosphino)xanthene with a bite angle of about 112 degrees. In run 2-6 the ligand used was Bis(2-(diphenylphosphino)phenyl)ether (DPEphos, with a bite angle of 102 degrees. In runs 2-7 through 2-12 the ligand used was DIOP.

From the data given above, the exceedingly high normal/iso product ratios obtainable are demonstrated. The catalyst systems employed in Runs 2-1 through 2-6 are believed to be a novel for the hydroformylation of allyl alcohol.

COMPARATIVE EXAMPLES

Referring to Japan Kokai 06-279344, Table 1, the liquid CO concentration was calculated using the inlet CO concentration rather then the log mean concentration in the above equation. Note that this gives a higher value for CO liquid concentration than the log mean concentration. The calculated CO concentration for each is 4.33 mg mols/l, well below the lower limit specified in accordance with the present invention. It can be seen from the data presented that the reproductibility of the runs deteriorated after only two repetitions.

We claim:

1. In the process for the hydroformylation of allyl alcohol by reaction with a mixture of CO and hydrogen in the liquid phase in the presence of a catalyst comprised of a rhodium complex and a bidentate diphosphine ligand, said ligand having a bite angle of 100–120 degrees, the improvement which comprises reducing the formation of saturated $C_3$ compounds by maintaining the concentration of CO in the liquid phase above 4.5 mg mols/liter during the hydroformylation.

2. The process of claim 1 wherein the concentration of CO in the liquid phase is maintained above about 5.0 mg. mols/liter during the hydroformylation.

3. The process of claim 1 wherein the bidendate diphosphine ligand is (isopropylindene-2,3-dihydroxy-1,4-diphenylphosphine)butane.

4. The process of claim 1 wherein the bidendate diphosphine ligand is 9,9-Dimethy-1-4,6-bis(diphenylphosphino)xanthene=Xantphos.

5. The process of claim 1 wherein the bidendate diphosphine ligand is 2,7-Di-tert-butyl-9,9- dimethyl-4,6-bis(diphenylphosphino)xanthene.

6. The process of claim 1 wherein the bidendate diphosphine ligand is bis(2-(diphenylphosphino)phenyl)ether.

* * * * *